United States Patent
Pitz et al.

(10) Patent No.: US 7,086,861 B2
(45) Date of Patent: Aug. 8, 2006

(54) SYSTEM FOR DISPENSING VISCOUS MATERIALS

(76) Inventors: Richard J. Pitz, 400 E. 54th St., New York, NY (US) 10022; Dan Vogel, 400 E. 54th St., New York, NY (US) 10022

(*) Notice: Subject to any disclaimer, the term of this patent is extended or adjusted under 35 U.S.C. 154(b) by 0 days.

(21) Appl. No.: 11/088,095

(22) Filed: Mar. 24, 2005

(65) Prior Publication Data

US 2005/0170313 A1  Aug. 4, 2005

Related U.S. Application Data

(63) Continuation-in-part of application No. 10/090,125, filed on Mar. 1, 2002, now abandoned.

(51) Int. Cl.
*A61C 5/04* (2006.01)

(52) U.S. Cl. ............................................. 433/90; 401/1
(58) Field of Classification Search .................. 433/90, 433/89; 401/1, 2; 222/146.5, 146.2
See application file for complete search history.

(56) References Cited

U.S. PATENT DOCUMENTS

| RE25,483 | E | * | 11/1963 | Lemos ........................ 604/20 |
| 3,364,577 | A | * | 1/1968 | Oakleaf et al. ............... 433/32 |
| 3,653,552 | A | * | 4/1972 | Ash ........................ 222/146.5 |
| 3,858,985 | A | * | 1/1975 | Fiveash ........................ 401/2 |
| 4,265,618 | A | * | 5/1981 | Herskovitz et al. ........... 433/32 |
| 4,391,590 | A | * | 7/1983 | Dougherty .................... 433/90 |
| 4,704,088 | A | * | 11/1987 | Newman ...................... 433/81 |
| 4,820,152 | A | * | 4/1989 | Warrin et al. ................. 433/86 |
| 5,100,320 | A | * | 3/1992 | Martin et al. ................. 433/90 |
| 6,041,972 | A | * | 3/2000 | Maayeh et al. ............. 222/173 |
| 6,230,936 | B1 | * | 5/2001 | Lasko ...................... 222/146.5 |
| 6,616,448 | B1 | * | 9/2003 | Friedman ..................... 433/32 |

* cited by examiner

*Primary Examiner*—Todd E. Manahan
(74) *Attorney, Agent, or Firm*—Epstein Drangel Bazerman & James, LLP.

(57) ABSTRACT

A cartridge-type system having a fluid containment in the cartridge which comprises a fluid containing body which is adapted to be attached to a delivery device, the body of the cartridge including preferably electrically energizable heating means, preferably energized through a delivery device, for heating the contents of the cartridge and thus enhancing their deliverability.

2 Claims, 7 Drawing Sheets

SYSTEM FOR DISPENSING VISCOUS MATERIALS

This application is based on previous application Ser. No. 60/343,081 bearing date Oct. 27, 2001 and is a continuation in part of our application Ser. No. 10/090,125 of Mar. 1, 2002 now abandoned entitled A System for Dispensing Viscous Materials.

BACKGROUND

This invention pertains generally to pressure actuated dispensers, applicators and devices for application of fluid materials, and more particularly to an apparatus which is part of a system which allows conventional dispensing devices to be adapted or modified such that a variety of materials in varying quantities may be dispensed from or applied by a single dispensing device.

Various types of dental materials are dispensed from some form of dispensing apparatus (Dragon U.S. Pat. No. 5,061,179). This may facilitate a more ergonomic action or in the case of dental composites, ease of placement. This placement may be enhanced visually by the apparatus or it may be used to overcome a drawback of the material itself. Such is the case with many of the light cured resins currently in use.

To increase strength, micron sized particles are incorporated into the resin such that when the composite is cured in the tooth, it is esthetically satisfactory and will be able to withstand the chewing forces. Today it is common to have filler content over 80%. Delivery of the material is commonly done with a hand actuated dispenser modified to magnify hand pressure as much as 5 times. Such dispensers are coupled with a cartridge filled with the appropriate material for the task. These cartridges usually are friction fit to the proximal end of the dispenser as a convenience factor. The cartridges are mostly uniform in their circumference, however their length may vary. The opening of the distal end contains a plug that when pushed along the longitudinal axis by part of the dispenser expresses the material from the proximal end of the cartridge. Such orifices may vary in size of opening and the length of the cannula that is part of the cartridge may also vary in length.

Owing to the resistance of flow by the very highly filled composites, the orifice of the cartridge can be greater than 3 mm. Multiple handheld devices that magnified the force necessary to overcome the resistance due to viscosity were patented (Kunkel, et al., U.S. Pat. No. 5,871,354). Patents on the size, shape and orifice opening of the cartridge were issued. In each case it was in overcoming the viscosity problem that drove the research. While the industry tried to market these combinations as convenience items, it noted that there was a problem of placing these materials so as not to have voids, incompletely cured resins and uncovered surfaces.

Dental composite materials are mixtures of liquid resins and suspended particles. Light wavelengths of sufficient energy to cause a reaction are introduced to allow the resin to cure producing a sufficiently strong material to withstand the chewing forces of the mouth. Many types of light sources are used but the nature of the material preclude the immediate setting throughout as with a two part chemical set resin system. The initial set starts at the area with the most intense light energy, creating a shrinkage as the material cures to the greatest mass. This occurs regardless of the intensity or wavelength of the light source.

This effect has led to open margins in the first instance which is entirely due to the chemistry of the material. In the second instance, the inability to deliver the material equally to all parts of the preparation, owing to its size, complex shape (angles, undercuts, etc), and location in the mouth are an operator shortcoming. The second instance may be attributed to the viscous nature of the material. The primary obligation of the procedure is to cover the margins such that a completely cured composite material leaves no gaps, voids or uncured material which may lead to recurrent decay.

To facilitate such coverage, reduce the total shrinkage to an acceptable level, and produce a completely cured resin, the manufacturers recommend a layering technique. Operator technique deficiency, owing to the viscous nature of the material, can incorporate voids that will alter the strength and optical properties of the cured material. To overcome the high probability of open margins, the industry introduced a flowable composite with more liquid resins and less filler. This material is placed at the interface of the tooth and retainer (should one be needed) or the floor and sides of the preparation. These flowable composites can be introduced with a cannula as small as 25 ga or smaller.

Again, these flowable composites were initially meant to close margins and reduce the overall shrinkage factor. Operator error is introduced in the use of these materials when bubbles are introduced by the manipulation of the cannula or when too much of the material is introduced into the preparation. More volatile diluents in the resins are incorporated to increase the flow (Klee, et al., U.S. Pat. No. 5,876,210, pps. 13, 14). This action reduces the strength and creates greater shrinkage. There is a decided increase in the vapor pressure that occurs when the material goes from room temperature (approximately 72° F.) to body temperature (98.6° F.), thereby creating tiny bubbles. Any area where there is oxygen present will create an oxygen inhibited layer causing uncured resin that remains uncured.

The overall intent of the manufacturers in their product and its delivery is to wet the surface of the tooth with the resin, primarily to help seal and have a homogeneous material against the tooth surface that will, when cured correctly, produce a restoration of sufficient strength to withstand the chewing forces to prevent breakage.

Patents have been issued that deal with the nature of all viscous materials, dealing with orifice openings, size and shape of the material carrier (cartridge, capsule) (Bender, U.S. Pat. No. 5,707,234), means of multiplying forces necessary to overcome the viscosity and size, shape and mechanical properties of the cartridge holder used to dispense such materials. None have been issued where the resistance to flow caused by the viscosity is overcome by applying controlled heat at the point of delivery (generating heat within the capsule itself). Such heat must be applied within a specific range to take advantage of the optimal flow given to the resin component of the mixture. Such heat range must not in any way alter the chemistry or any of the other desirable properties of the material when in a plastic state or when converted to a cured state.

This invention overcomes all the disadvantages of forcing a viscous material through a small opening by altering the plasticity of a mixture by applying controlled heat allowing a component of the mixture to become fluid.

The advantages to such a method and delivery system include: (1) reduction of voids owing to more consistent placement due to increased flow; (2) greater wetting of the surface of the tooth with the resins in a more liquid state; (3) ease of delivery (a) less force required (b) smaller delivery tips for better visualization; (4) less volatile diluents required, yielding grater strength and less shrinkage; (5) use of longer chain resins for greater strength; (6) ability to incorporate a filler content to 90% and above without compromising the flow using a standard dental hand delivery syringe; (7) the manipulation of the chemistry of the resins such that heating within controlled parameters will deliver the appropriate delta energy to initiate a self-cure; and (8) allow for a two-component system to exist in a premixed state in the same cartridge without setting or degrading prior to intended use until the appropriate delta energy is applied.

SUMMARY OF THE INVENTION

The invention provides for a delivery system where a viscous material such as dental composite is heated by an induction field or by resistance to an electric current. The system comprises at the proximate end a capsule-like cartridge that is self-heating. The capsule may be fabricated of any number of heat conducting polymers or doped polymers that are susceptible to induction fields or any material that will heat when an induction current is applied. In the second instance the capsules may have a resistance wire of the appropriate metal or any other material to allow heating of the capsule when a current is applied. In the third instance the capsule may have an induction coil embedded in its wall combined with any type of metal or other material where this becomes the heating device when current of the appropriate nature is applied. In the fourth instance a thin film or foil may be applied to either the outer surface or the inner surface of the capsule such that when a current is applied the foil or film heats and in so doing heats the capsule and the contents.

Coupled with the above described capsule is a delivery device. This hand held device whether powered manually or electrically forces a shaft to engage a piston embedded within the cartridge to move forward, dispensing the material within the cartridge at its proximal end. In the manually powered mode an electrical power source, whether a battery, capacitor discharge or AC/DC current, is used exclusively to activate the various heating methods described above. In the electrically powered mode, a linear stepper motor or other such motor with a proper configuration allows the shaft to engage the piston embedded in the cartridge and allow the material contained within the cartridge to be dispensed at its proximal end. In the electrically powered configuration the power source described above is used to power the motor as well as the energy to activate the various heating elements described above. In addition such device may have the induction coil embedded in the barrel extension of the device in such placement as to provide adequate heating of the capsule. We have found it very effective that the induction coil heat the piston, which therefore may be made in whole or in part of material such as iron which, when subjected to electromagnetic energization.

The present invention is system and carrier for the delivery of dental materials, primarily composite materials (but not limited to such materials), where the viscosity of the material is changed and other properties of the material is enhanced by the addition of a controlled heat.

The system and carrier is located at the proximal end of a hand held syringe (placement device) that provides, either by digital manipulation or a linear step motor or other type electrical motor, a force necessary to deposit a determined amount of a dental material (composite) into the tooth preparation. The placement device is electrically powered, either by battery or AC current, to activate in the first instance an induction coil that will cause the carrier of the material to heat, thereby reducing the viscosity prior to placement. In the second instance the carrier (carpule) itself is the resistance to the current thereby heating the carrier, reducing the viscosity of the material in the carrier prior to placement.

The carriers of the materials (carpules) can be of any size and shape such that it be of an advantageous nature to allow for the proper visualization. Many types of standard carpules are available to fit various handles (syringes, "guns"). Most of these carpules hold approximately ½ gram of a light-cured composite. Various materials currently on the market will allow a standard polymer material to be manufactured to meet the specifications allowing the temperature of the carpule to be raised over a carefully selected temperature.

Advantages of the heatable carpules (and or carrier of any size) is that the need for multiple types of composite materials is eliminated. One very highly filled material will suffice. The orifice openings of the carpule can be reduced, such that more accurate placement of the material can be accomplished. The properties of the resin are enhanced from both a chemical standpoint and their ability to wet the tooth surface. Strength and optical properties are enhanced by allowing a much higher filler content unencumbered by the detrimental viscosity to such materials. Adding controlled heat at the point of placement will allow different chemical composition to be manufactured such that the composite material can be manufactured where a two part resin can be incorporated into the same carrier and by adding additional energy (delta 2) a dual cure can be accomplished (chemical and light cure). Since the carpules may be made of a standard size, they can be used without the enhanced embodiment in the standard syringes available on the market.

Of particular importance is the necessity of having a continuous, controlled heat of the material, especially at the orifice. This is to overcome the rapid cooling of the extruded material. Composites by their nature have a low specific heat. Previous methods while using heat sources failed to recognize the nature of the material, such that over time continuous heating will alter the chemistry of the composite resin. This alteration will produce a material that becomes lumpy or produces aggregate particles that will alter the finished product. This is evidenced by altered color, strength and wear characteristics.

The advantage of the method in this application is rapid heating to a precisely controlled heat content of the material with rapid delivery such that the physical and chemical properties are not altered.

DETAILED DESCRIPTION OF PREFERRED EMBODIMENTS

The present invention will now be disclosed in detail with the aid of the embodiment of FIGS. 1 through 7.

Figure 1:
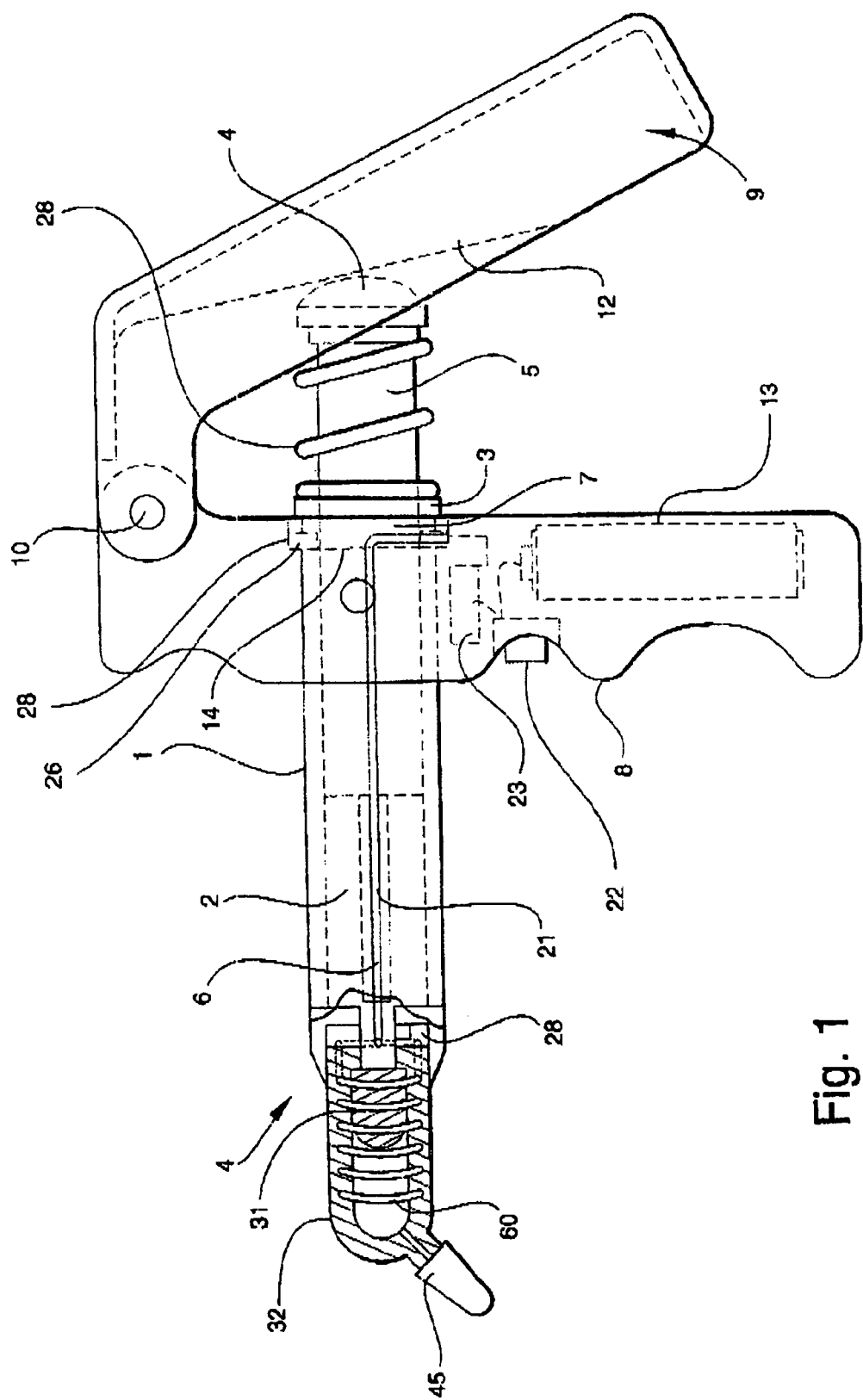
FIG. 1 is a side elevation of the dispensing device and cartridge that comprises the system in accordance with the present invention.

FIG. 1 shows an ejector holder of a type especially designed to hold in an operative position a cartridge in conjunction to form a system that embodies the principles of the present invention. The holder comprises a barrel (1) having an interior bore (2) extending from a rearward end (3) toward the forward end (4) thereof for receiving a plunger (5) of the same diameter as that of the interior bore (2) for the major portion of the length of the plunger. The forward end of the plunger has a smaller diameter extension (6).

Figure 3:
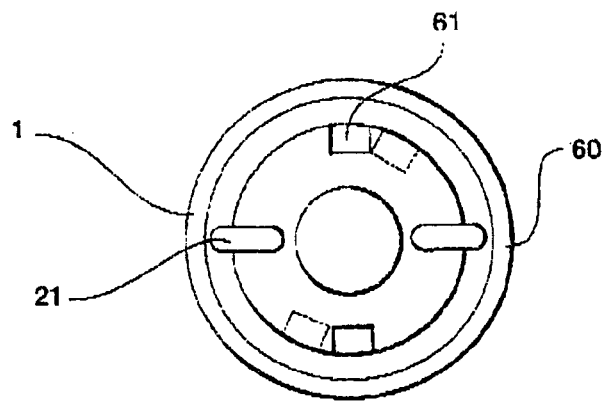
FIG. 3 is a cross sectional view of the rear of the cartridge showing the electrical connections and the recesses for the mechanical connections of the cartridge with the proximal end of the barrel of the dispensing device.
Figure 4:
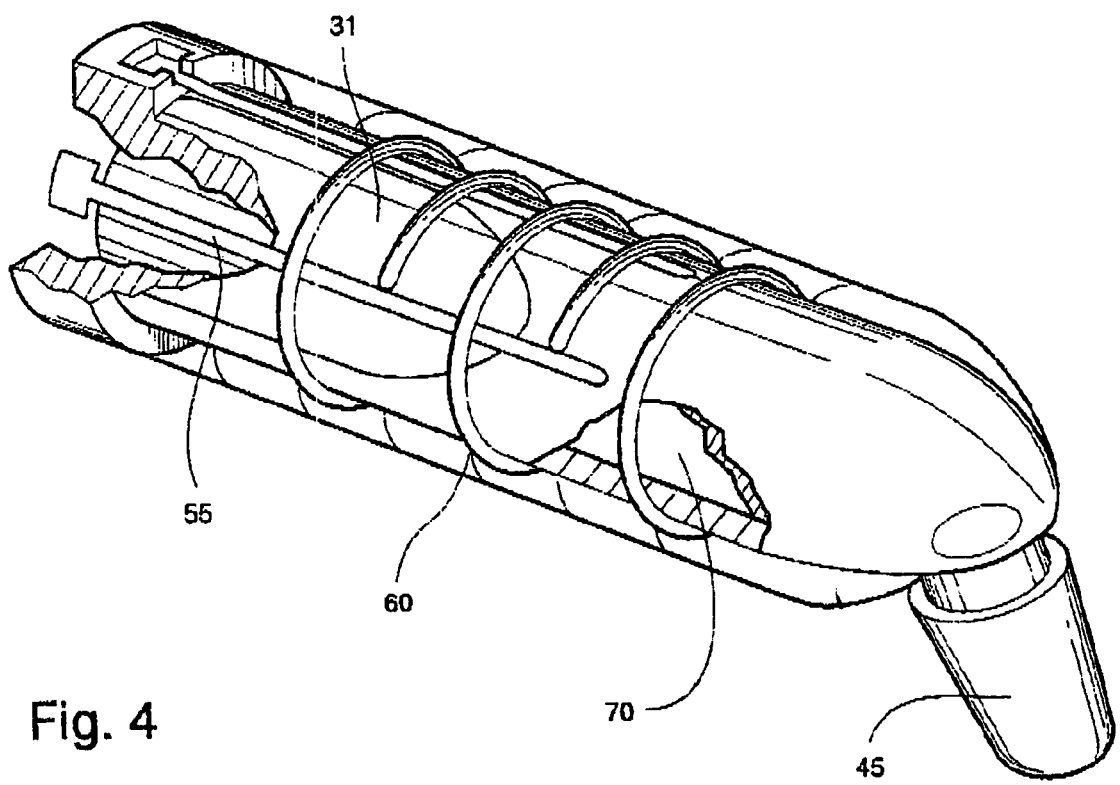
FIG. 4 is an angular view, partly broken away, of the cartridge showing the embedded metal ribs of one of the preferred cartridges in accordance with the invention.
Figure 5:
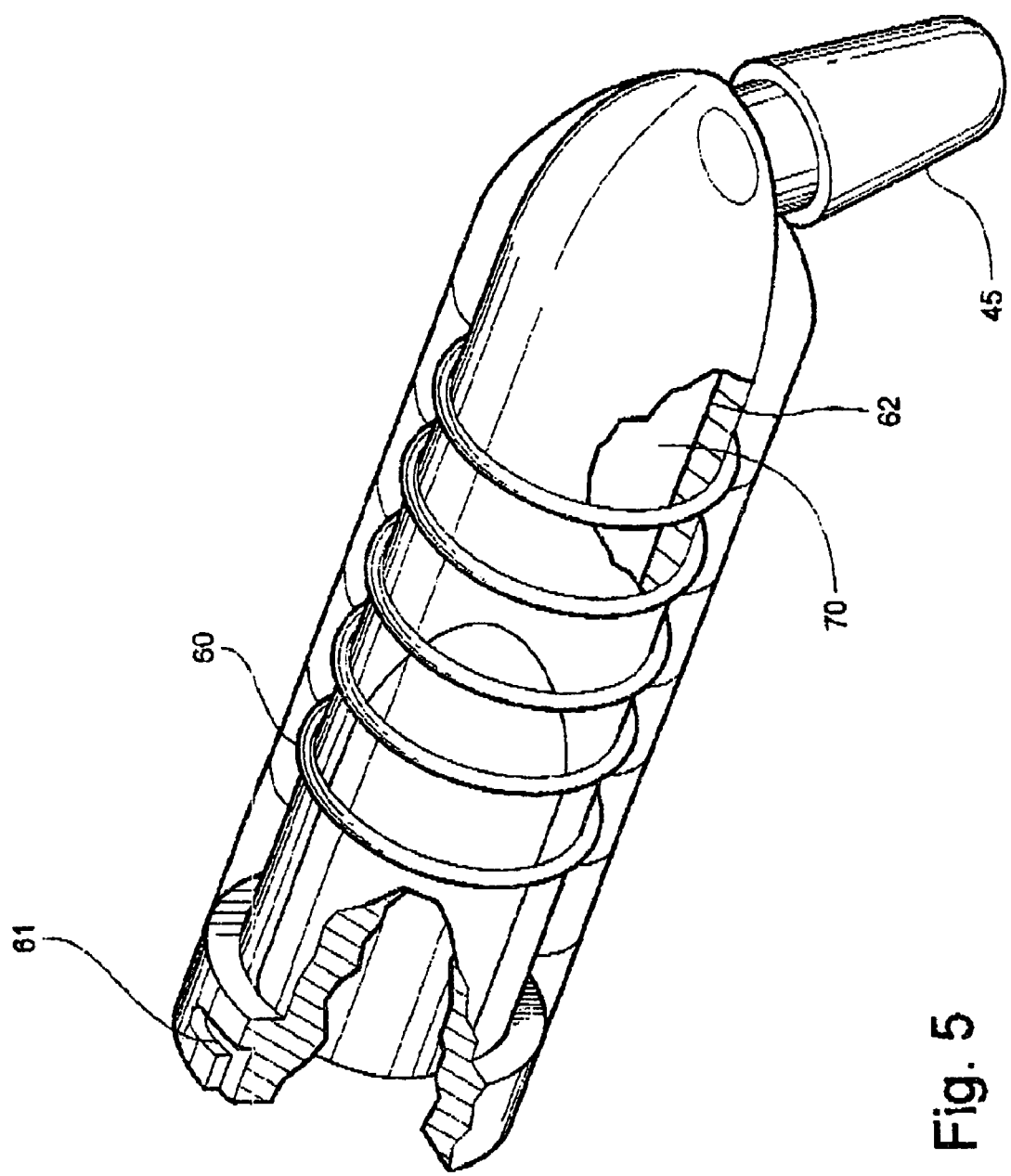
FIG. 5 is an angular view, partly broken away, showing the embedded resistance coil along with the electrical connection, and mechanical connection, as one embodiment of the cartridge in accordance with the invention.
Figure 6:
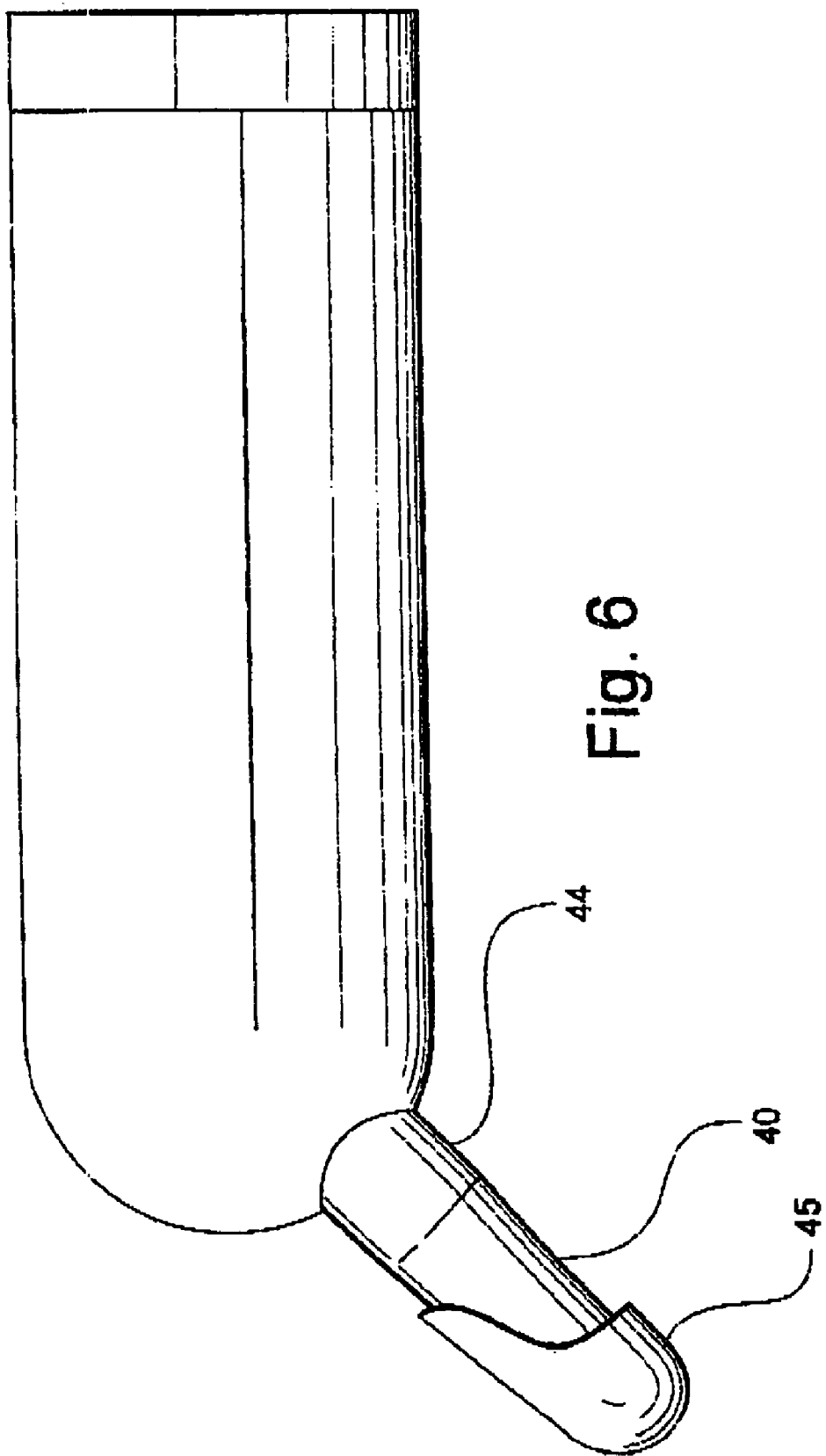
FIG. 6 is a side elevational view of the cartridge.
Figure 7:
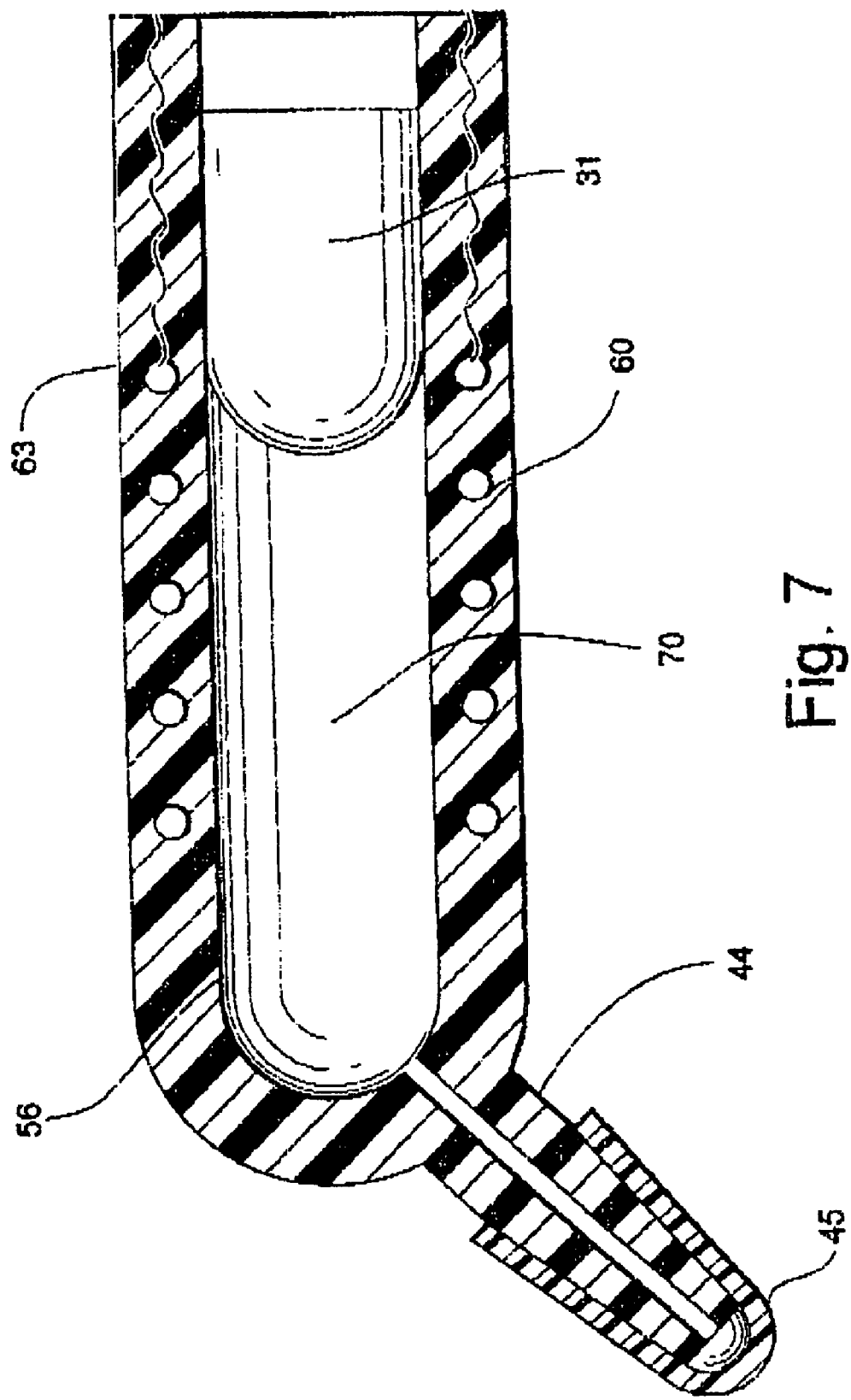
FIG. 7 is a cross-sectional view of the cartridge.

The rearward end (3) of the barrel (1) extends through the handle member (8). The barrel (1) has a flange (7) that is located in a recess of the handle (8) that is perpendicular to the barrel (1). The barrel is then free to rotate within this recess (14). Connected to the flange (7) of the barrel (1) is an electrical connection (26) such that when the barrel (1) is rotated the electrical connection is not compromised. The proximal end of the barrel ends in forward bulkhead (15) that allows the forward end of the plunger (2) to pass through. The bulkhead is of such thickness as to allow for an electrical connection to electrical leads (21) running longitudinally from the electrical connection (50) at the proximal end of the barrel to the distal flange (7) with the associated electrical connection (26). The proximal end of the barrel (1) has forward extensions such as to engage recesses (61) located in the distal face of the cartridge (32) as shown in FIGS. 3 and 5, in such a configuration that these mated extensions and recesses (61) when rotated in the proper direction will give a positive seat between the anterior portion of the bulkhead (15) and the flat portion of the distal end of the cartridge (28).

Figure 2:
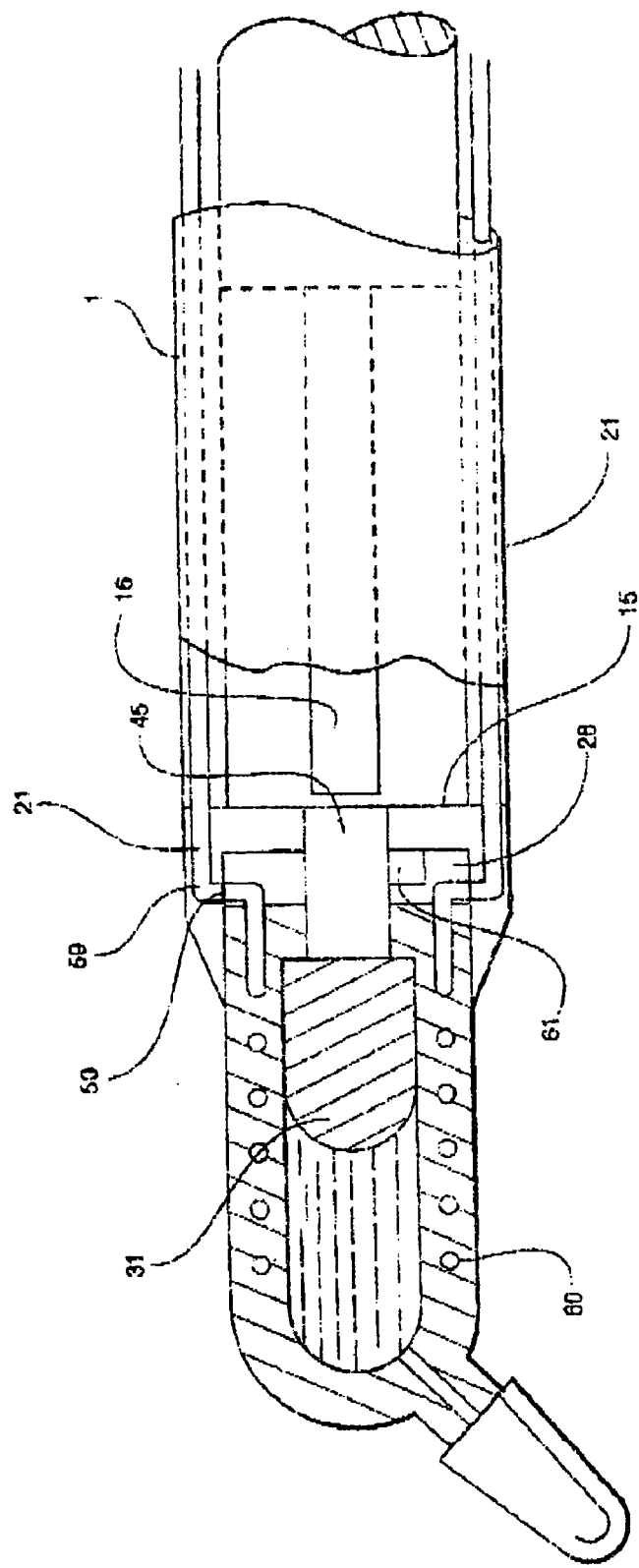
FIG. 2 is a fragmentary enlarged top view of the anterior portion of the connection of the dispensing device with the cartridge.

The cartridge (32) has an electrical connection (50) which mates with a concomitant connection in the bulkhead (15) of barrel (1) as shown in FIG. 2. The cartridge (32) has an embedded coil (60) as shown in FIGS. 1 and 2. The cartridge (32) mates with the barrel (1) at its proximal end which contains a bulkhead (15) allowing for a strong connection of the combined member to become a part of a rotating, electrically conductive component attached to a handle (8).

The handle (8) is pivotally connected to an operating lever (12) through a pivot pin (10) located at the upper end of the handle (9) and the operating lever (12) that is offset laterally to facilitate the operation of the lever (12) with respect to the outer end of the plunger (8) which terminates in a button (11) engaged by the inner surface (12) of the operating lever.

A coiled spring (28) surrounds the distal portion of the plunger between the forward handle (8) and the button (11) for purposes of extracting the plunger (5) when the operating lever (9) is released, following ejection of material from the cartridge (32).

The handle (8) contains an appropriate electrical source (13) such as a battery or capacitor discharge device and/or connection to an electrical outlet through a connecting cable. The handle (8) contains an on/off switch (22) connected to the electrical source (13) in conjunction with a temperature controller device (23) through a feedback thermocouple contained within or on the surface of the cartridge (60) (55).

Figure 2A:
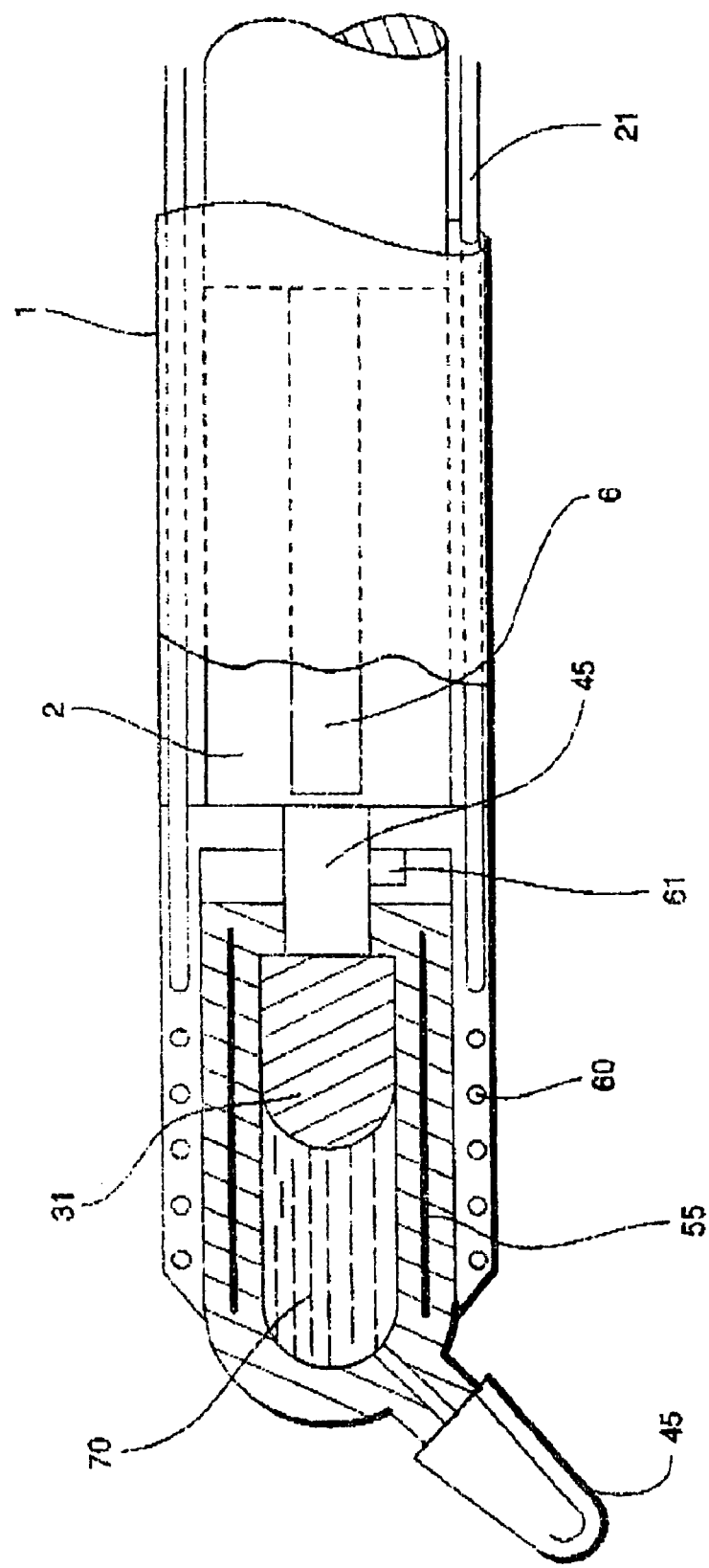
FIG. 2A is a view similar to FIG. 2, but showing an alternative embodiment.

The cartridge (32) which in conjunction with the dispensing device comprises the system is located at the proximal end of the barrel (1). The cartridge (32) is preferably formed by molding from a rigid synthetic resin or plastic material by means of a suitable mold. The intermediate body portion of the capsule (63) as shown in FIG. 5 for connection to the barrel (1) projections and also has electrical connections (50) that mate with similar connections (59) in the connecting face of the barrel (1). The cartridge is of sufficient thickness (62) to allow for an appropriate placement and configuration of a wire (60) that may be a coil but not limited to such configuration that when an electrical current is passed through creates a rise in temperature through resistance in one method and induction in the second method. The capsule (32) has a thermocouple device (55) to allow for a feedback mechanism to control the temperature of the material in the cartridge (70). Horizontal metal ribs (55) located in a longitudinal direction within the cartridge walls beneath the induction coil (60) become hot when subjected to the proper current and also act as a thermocouple (55) in a form of the invention. In another form of the invention, the barrel (1) is extended to cover the cartridge (32) which contains only the horizontal metal ribs (55) and no induction coil (60). The induction coil (60) is located in the barrel (1) as shown in FIG. 2A at the extended end and the electrical connection is with a direct wire (21) to the distal portion of the barrel (1) and connected to an on/off switch connected to the temperature feedback mechanism.

The body of the cartridge (63) extends forward in a uniform manner to a hemispherical closed end with an opening into an angularly placed discharge nipple (40), the opening of which is preferably a very fine dimension of small diameter. To effect the ejection of material from the cartridge (32) such as dental filling material, cement, or other viscous material and the like, for example, the cartridge (32) includes a piston (31) as shown in FIG. 2, and the inner end thereof also is hemispherical and complementary to the interior of the closed end of the cartridge. Without restriction thereto, the outer end of the piston may be flat for encasement, for example in FIG. 2 where the proximal end of plunger (5) is moved forward by actuation of the operating lever (9).

Removal of the cartridge (32) from the proximal end of the barrel is accomplished by turning in the appropriate direction allowing the connecting tangs on the proximal end of the barrel (15) to disengage from the female connection (61) in the distal end of the cartridge (28).

From the foregoing, it will be seen that the proximal end of the barrel (15) is especially adapted to receive the particular type cartridge (32) to be used therewith, which is a subject of the system in this application. This does not limit the connecting mechanism to the one previously described but only to demonstrate the necessity of having a positive connection to allow for a secure tight seal and positive electrical conductivity. The connection is very simple, highly effective design to permit a sure and effective adaptation and release.

The cartridge (32) comprising part of the method and the system of the invention not only is capable of serving as receptacle for material to be discharged when filled for example, from storage supply, but, even more importantly, the cartridge can be filled at a factory with predetermined quantities of material, by automatic machinery, and sealed therein by application of the piston (31) which, under the circumstance, serves as a closure for the cartridge. The above described design particularly facilitates such operations. Further, during filling, air in the cartridge in advance of the material can be discharged through the nipple (44) until filled and then the open end of the nipple may be suitably and inexpensively closed by suitable seal means, such as a small piece of sheet material having pressure sensitive cement on one side and placing said piece across the nipple in any suitable manner.

In accordance with the invention, a further improved feature for the cartridge comprises providing a preferably cup-shaped cap (45) which is of a suitable shape either to frictionally engage the tip portion of the nipple (44) or either the cap or nipple, or both to secure the cap releasably upon the tip of the nipple in sealed manner. Cap (45) has an outer flange position adjacent to the opening of the cap. In closed position, the inner surface of the cap (45) is retained by the nipple with a force sufficient to slightly bend the wall of the cap. This creates enough friction to allow for a secure closure and also allows for easy removal prior to its intended use.

Moreover, the cap (45) serves an important additional feature in that, in addition to sealing the contents of the cartridge in conjunction with the piston (31), the cap may be color coded to any number of purposes, weight or quantity of the material therein, setting time, and otherwise.

Also the body of the cartridge as well as the cap (45) and piston (31) may all be molded from a similar plastic material which is colored suitably to render the items opaque or otherwise impervious to the transmission of ambient light which, if the contents are subject to being set by such light, prevents premature setting thereof.

In an alternate, and preferred, embodiment the wire 60 defines an induction coil and the piston 31 is formed at least in part of material such as iron which, when subjected to a varying electromagnetic field, will become heated and transfer heat to the cartridge contents.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. A cartridge for storing and dispensing a viscous medicinal fluid comprising a body having lower, upper and mid-portions and defining a cavity in which a viscous medicinal fluid may be stored, said lower portion of said cartridge having an outlet opening communicating with said cavity through which said fluid may pass, a piston slideable in said cartridge cavity from said upper portion into at least said mid-portion of said body, said upper portion of said cartridge defining an external opening communicating with said cavity, and comprising means at its upper portion for engaging a delivery device having a moveable pusher and mounting said cartridge thereon so that said moveable pusher may pass through said external opening into said cavity and engage and move said piston, and heating means carried by said cartridge which when energized, heats the fluid in said mid-portion of said cartridge, in which said heating means comprises an introduction coil mounted on said cartridge body and at least part of said piston comprises material which will become heated when subjected to the action of said induction coil.

2. The cartridge of claims 1 in combination with an electrically energized delivery device on which said cartridge may be moved, said cartridge and delivery device having external electrical terminals which operatively engage when said cartridge is mounted on said delivery device, thereby to energize said heating means from said delivery device.

* * * * *